US012643106B2

(12) United States Patent
Inoue

(10) Patent No.: US 12,643,106 B2
(45) Date of Patent: Jun. 2, 2026

(54) BIOLOGICAL SAMPLE STORAGE TUBE CAP, AND BIOLOGICAL SAMPLE STORAGE CONTAINER EQUIPPED WITH SAME

(71) Applicant: KITAZATO CORPORATION, Fuji (JP)

(72) Inventor: Futoshi Inoue, Fujinomiya (JP)

(73) Assignee: KITAZATO CORPORATION, Fuji (JP)

( * ) Notice: Subject to any disclaimer, the term of this patent is extended or adjusted under 35 U.S.C. 154(b) by 565 days.

(21) Appl. No.: 18/174,893

(22) Filed: Feb. 27, 2023

(65) Prior Publication Data

US 2023/0211346 A1 Jul. 6, 2023

Related U.S. Application Data

(63) Continuation of application No. PCT/JP2021/030477, filed on Aug. 19, 2021.

(30) Foreign Application Priority Data

Aug. 31, 2020 (JP) ................................. 2020-146184

(51) Int. Cl.
*B01L 3/00* (2006.01)
*A61B 10/00* (2006.01)
(Continued)

(52) U.S. Cl.
CPC ........... *B01L 3/50825* (2013.01); *A61B 10/00* (2013.01); *B01L 2200/025* (2013.01); (Continued)

(58) Field of Classification Search
None
See application file for complete search history.

(56) References Cited

U.S. PATENT DOCUMENTS 4,175,008 A 11/1979 White
4,653,510 A * 3/1987 Koll ........................ A61B 10/04
600/572
(Continued)

FOREIGN PATENT DOCUMENTS

JP 2006-223168 A 8/2006
JP 2009-226245 A 10/2009
(Continued)

OTHER PUBLICATIONS

International Search Report of PCT/JP2021/030477 mailed Sep. 28, 2021.
(Continued)

*Primary Examiner* — Henry H Nguyen
(74) *Attorney, Agent, or Firm* — Muncy, Geissler, Olds & Lowe, P.C.

(57) ABSTRACT

A biological sample storage container includes a biological sample storage tube and a biological sample storage tube cap. The tube cap is a cap that is to be attached to the tube having a lower closed portion and an upper opening portion, and is for closing the upper opening portion. The tube cap includes a main body portion that enters the upper opening portion of the biological sample storage tube and closes the upper opening portion, an elongated biological sample adhering portion that extends downward from a lower face of the main body portion, and a flange that protrudes laterally outward from the main body portion. The biological sample adhering portion is cuttable and falls into the biological sample storage tube after being cut.

17 Claims, 10 Drawing Sheets

(51) Int. Cl.

| | | |
|---|---|---|
| *C12M 1/00* | (2006.01) | |
| *C12M 1/30* | (2006.01) | |
| *G01N 1/02* | (2006.01) | |
| *G01N 1/28* | (2006.01) | |

(52) U.S. Cl.

CPC ... *B01L 2300/021* (2013.01); *B01L 2300/042* (2013.01); *B01L 2300/0832* (2013.01); *C12M 1/30* (2013.01); *C12M 23/38* (2013.01); *C12M 33/02* (2013.01); *G01N 2001/028* (2013.01); *G01N 2001/2833* (2013.01)

(56) References Cited

U.S. PATENT DOCUMENTS

| | | | | |
|---|---|---|---|---|
| 5,225,165 A * | 7/1993 | Perlman | ................ | B01L 3/5021 422/550 |
| 5,722,553 A * | 3/1998 | Hovatter | .............. | B01L 3/5085 220/23.8 |
| 2008/0145272 A1* | 6/2008 | Feaster | ................ | B01L 3/5023 422/69 |
| 2011/0053208 A1 | 3/2011 | Reiss | | |
| 2014/0017147 A1* | 1/2014 | Kim | ................... | B01L 3/50825 422/501 |
| 2014/0287955 A1 | 9/2014 | Wende et al. | | |
| 2014/0342371 A1* | 11/2014 | Holmes | ........... | A61B 5/150343 435/7.1 |
| 2017/0065215 A1* | 3/2017 | Piacentini | ........ | G01N 33/48771 |
| 2017/0095816 A1 | 4/2017 | Rida | | |
| 2020/0256863 A1 | 8/2020 | Toei | | |
| 2021/0229086 A1* | 7/2021 | Esteves Reis | ...... | B01L 3/50273 |

FOREIGN PATENT DOCUMENTS

| | | | |
|---|---|---|---|
| JP | 2014-533934 A | 12/2014 | |
| JP | 2017-147984 A | 8/2017 | |
| JP | 2019-080549 A | 5/2019 | |
| JP | 2019-176829 A | 10/2019 | |
| KR | 20060005535 | 1/2006 | |
| WO | WO-03068398 A1 * | 8/2003 | ......... A61B 10/0038 |

OTHER PUBLICATIONS

International Preliminary report on Patentability of the corresponding international application No. PCT/JP2021/030477 Issued Feb. 28, 2023, which includes Written opinion of PCT/JP2021/030477 mailed Sep. 28, 2021.

Supplementary European Search Report of the corresponding EP 21861401 mailed Jan. 29, 2024.

* cited by examiner

BIOLOGICAL SAMPLE STORAGE TUBE CAP, AND BIOLOGICAL SAMPLE STORAGE CONTAINER EQUIPPED WITH SAME

TECHNICAL FIELD

The present invention relates to a biological sample storage tube cap and a biological sample storage container provided with the same.

BACKGROUND ART

Biological sample analyses in biomedicine and molecular cell biology, for example, the detection and analysis of the chromosomal status of an embryo using a blastocyst culture medium, are performed. In in vitro artificial insemination, an ovum is collected from the mother's womb and fertilized in vitro with the father's sperm, the fertilized ovum is grown in an in vitro culture medium until it becomes a blastocyst, and the blastocyst is then implanted in the mother's uterus. However, for various reasons, fetal birth may not occur after the blastocyst is transferred to the uterus.

Chromosomes in the fertilized ovum originate from the maternal ovum and the paternal sperm, and a chromosomal abnormality in either the ovum or sperm leads to a chromosomal abnormality in the fertilized ovum. Each germ cell of a fertilized ovum from a healthy individual has 44 autosomes, i.e., 22 pairs of autosomes, and 2 sex chromosomes (XY in males, and XX in females). In the case of aneuploidy, all or some chromosomes may be a monoploid or polyploid chromosome, where the number of chromosomes are respectively lower or higher than that of a diploid chromosome.

In recent years, the chromosomal status of an embryo cultured in vitro is detected through preimplantation genetic screening (PGS). In preimplantation genetic screening, cells are collected from in vitro cultured embryos or biological samples associated with in vitro cultured embryos are collected, and chromosomes are analyzed using the collected cells or samples.

Although FISH (Fluorescence in Situ Hybridization) and PCR (Polymerase Chain Reaction) are used in chromosome testing, recent years has seen PCR become the mainstream. Many analyses such as genome analysis are performed as biological sample analyses in biomedicine and molecular cell biology.

In order to perform biological sample analyses in biomedicine and molecular cell biology as described above, a biological sample to be analyzed needs to be collected and reliably stored in a biological sample storage container.

Examples of a biological sample storage container include a biological sample storage container disclosed in Patent Document 1 (JP 2009-226245A). In the container (a microtube for PCR) disclosed in Patent Document 1, a reagent is introduced into the tube such that a sample containing DNA to be amplified adheres to a lid or a wall surface of the tube. Then, the reagent and the sample are mixed or stirred in the tube closed with the lid, and a specific DNA (DNA fragment) is amplified by repeating a cycle at a predetermined temperature.

PRIOR ART DOCUMENTS

Patent Documents

Patent Document 1: JP 2009-226245A

SUMMARY OF INVENTION

Technical Problem

A biological sample may not be appropriately stored in the above tube disclosed in Patent Document 1 (the sample may not adhere to the lid or the wall surface of the tube, or the adhered sample may come loose when the lid is attached), and in such cases, appropriate analysis or test results cannot be obtained.

It is an object of the present invention to provide a biological sample storage tube cap for allowing a biological sample to be reliably and easily stored in the tube and biological sample storage container provided with the same.

Solution to Problem

The following is provided as means for achieving the above-described object.

A biological sample storage tube cap comprises a main body portion; an elongated biological sample adhering portion that extends downward from a lower face of the main body portion; and a flange that protrudes laterally (or radially) outward from the main body portion, wherein the biological sample storage tube cap is to be attached to a hollow biological sample storage tube having a lower closed portion and an upper opening portion, and that is for closing the upper opening portion, the main body portion is configured to enter the upper opening portion of the biological sample storage tube and close the upper opening portion, and the biological sample adhering portion is enterable in the biological sample storage tube and cuttable and a cut piece formed by cutting of the biological sample adhering portion can fall into the biological sample storage tube.

The following is provided as another means for achieving the above-described object.

A biological sample storage container comprises a hollow biological sample storage tube having a lower closed portion and an upper opening portion; and a biological sample storage tube cap for closing the upper opening portion, and the biological sample storage tube cap is the above biological cal sample storage tube cap.

DESCRIPTION OF EMBODIMENTS

Figure 1:
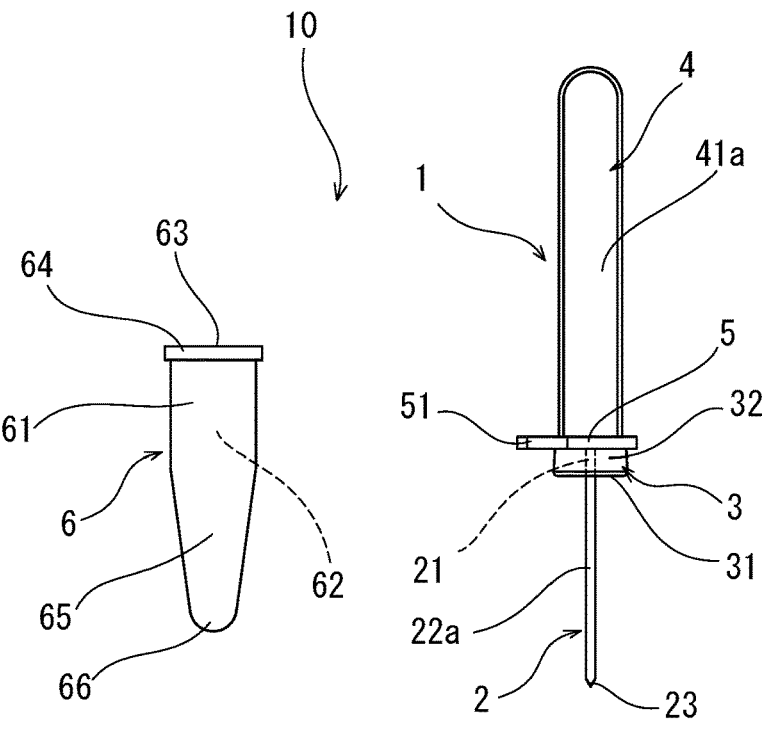
FIG. 1 is a front view of a biological sample storage container provided with a biological sample storage tube cap according to the present invention.
Figure 2:
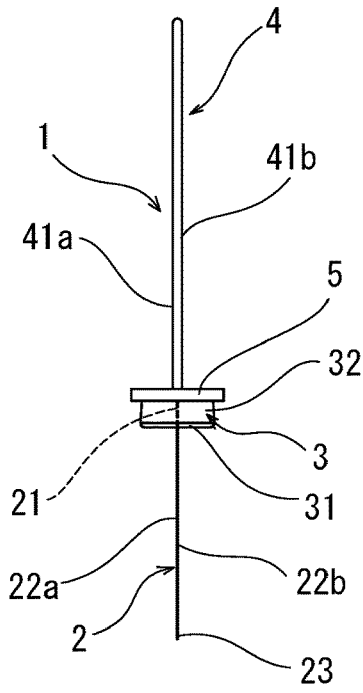
FIG. 2 is a right side view of the biological sample storage tube cap shown in FIG. 1.

The biological sample storage tube cap according to the present invention and the biological sample storage container provided with the same will be described with reference to examples illustrated in the drawings.

A biological sample storage tube cap 1 according to the present invention comprises a main body portion 3, an elongated biological sample adhering portion 2 that extends downward from a lower face of the main body portion 3, and a flange 5 that protrudes laterally outward from the main body portion. The biological sample storage tube cap is to be attached to a hollow biological sample storage tube 6 having a lower closed portion 66 and an upper opening portion 63, and that is for closing the upper opening portion 63, the main body portion 3 is configured to enter the upper opening portion 63 of the biological sample storage tube 6 and close the upper opening portion 63, and the biological sample adhering portion 2 is enterable in the biological sample storage tube 6 and cuttable and a cut piece formed by cutting of the biological sample adhering portion 2 can fall into the biological sample storage tube 6.

Also, a biological sample storage tube cap 1 according to the present invention is a cap that is attached to a hollow biological sample storage tube 6 having a lower closed portion 66 and an upper opening portion 63, and that is for closing the upper opening portion 63. The biological sample storage tube cap 1 includes a main body portion 3 that enters the upper opening portion 63 of the biological sample storage tube 6 and closes the upper opening portion 63, an elongated biological sample adhering portion 2 that extends downward from a lower face of the main body portion 3, and a flange 5 that protrudes laterally outward from the main body portion 3. The biological sample adhering portion 2 is cuttable and falls into the biological sample storage tube 6 after being cut.

Further, as shown in FIG. 1, the biological sample storage container 10 according to the present invention includes the hollow biological sample storage tube 6 having the lower closed portion 66 and the upper opening portion 63, and the biological sample storage tube cap 1 for closing the upper opening portion 63, and the above mentioned biological sample storage tube cap 1 is used.

The biological sample storage container 10 according to the present invention is particularly effective when the biological sample storage tube 6 is a sample storage tube 6 for testing chromosomes of an in vitro fertilized ovum, and the biological sample adhering portion 2 is a cell adhering portion for a cell derived from the in vitro fertilized ovum.

Further, the biological sample storage container 10 according to the present invention is particularly effective when the biological sample storage tube 6 is a biological sample storage tube 6 for PCR, and the biological sample adhering portion 2 is a biological sample adhering portion 2 for PCR.

Figure 6:
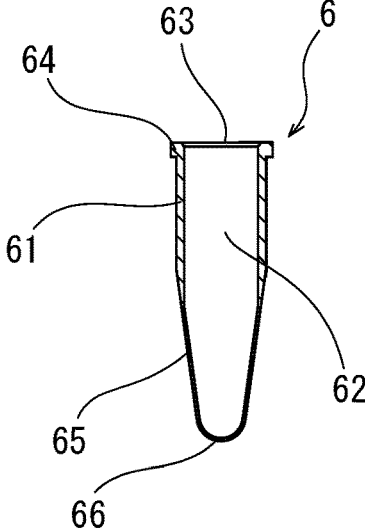
FIG. 6 is a longitudinal cross-sectional view of the biological sample storage tube shown in FIG. 1.

As shown in FIGS. 1 and 6, commercially available microtubes and PCR tubes are used as the biological sample storage tube 6 used in the biological sample storage container 10 according to the present invention.

As shown in FIGS. 1 and 6, the biological sample storage tube 6 has the lower closed portion 66 and the upper opening portion 63, and is a tubular member provided with an open upper end, and has an inner storage space 62. The tube 6 includes a cylindrical portion 61 that extends downward from the upper end opening portion 63, a tapered portion 65 that extends from the cylindrical portion 61 to the lower closed portion 66, and an annular rib 64 formed on a side face of the upper opening portion 63. Also, a bottom face of the lower closed portion 66 is a hemispherical closed portion. Further, an upper end-side face of the tube 6 is provided with the annular rib 64 that protrudes outward. Thus, the tube 6 is thickest at the upper opening portion 63 that has the annular rib 64.

The biological sample storage tube 6 with a volume of 0.1 to 2 ml is suitably used. So-called PCR tubes generally have a volume of 0.1 ml to 0.6 ml, and so-called microtubes generally have a volume of 0.5 ml to 2 ml.

Hard resin or semi-hard resin is suitable as a material of the biological sample storage tube 6, and in particular, it is desirable that the material thereof is transparent so that the inside of the tube 6 can be seen. Specifically, it is preferable to use, as a material of the biological sample storage tube 6, polyolefins such as polypropylene and polyethylene, styrene-based resins such as polystyrene and SBS, polyester resins such as polyethylene terephthalate and polybutylene terephthalate, acrylonitrile-based resins, polyvinyl chloride, PMMA (polymethyl methacrylate), and the like.

The biological sample storage tube cap 1 according to the present invention is a cap that is attached to the hollow biological sample storage tube 6 having the lower closed portion 66 and the upper opening portion 63, and that is for closing the upper opening portion 63. The biological sample storage tube cap 1 includes the main body portion 3 that enters the upper opening portion 63 of the biological sample storage tube 6 and closes the upper opening portion 63, the elongated biological sample adhering portion 2 that extends downward from the lower face of the main body portion 3, and the flange 5 that protrudes laterally outward from the main body portion 3. The biological sample adhering portion 2 is cuttable and falls into the biological sample storage tube 6 after being cut.

As shown in FIGS. 1 to 5, the biological sample storage tube cap 1 includes the main body portion 3 that enters the upper opening portion 63 of the biological sample storage tube 6 and closes the upper opening portion 63, the elongated biological sample adhering portion 2 that extends downward from a lower face 31 of the main body portion 3 and can be stored in the tube 6, the flange 5 that protrudes laterally outward from the main body portion 3, and a biological sample associated information presenting plate-shaped portion 4 that extends upward from the upper face of the main body portion 3 by a predetermined length.

As shown in FIGS. 1 to 5, the main body portion 3 has a short columnar or cylindrical shape, and is able to enter the tube 6 via the upper opening portion 63. Also, in this example, the lower end portion of the main body portion 3 has an outer diameter that is substantially the same as or slightly larger than the inner diameter of the upper opening portion 63 and the cylindrical portion 61 of the tube 6. Thus, as a result of the main body portion 3 entering the tube 6, the opening portion of the tube 6 is closed in a liquid-tight state and an air-tight state.

Figure 4:
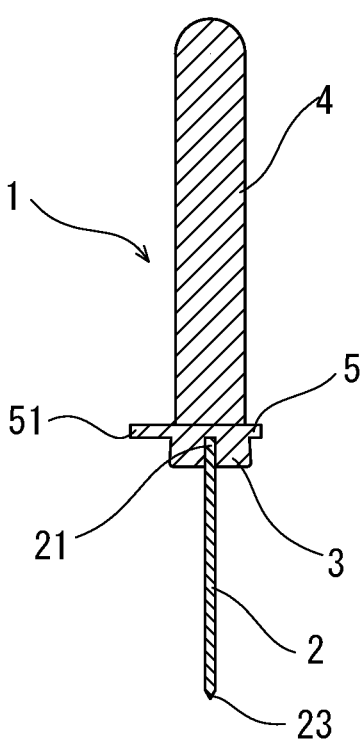
FIG. 4 is a cross-sectional view taken along line A-A in FIG. 3.
Figure 5:
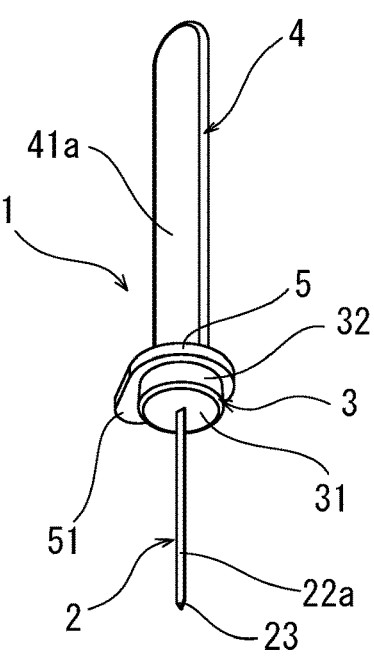
FIG. 5 is a perspective view of the biological sample storage tube cap shown in FIG. 1 when viewed from below.

Further, as shown in FIGS. 1 and 4, in the cap 1 of this example, the main body portion 3 has a short columnar or cylindrical shape, and the diameter of the main body portion 3 increases toward the leading end thereof. Specifically, the lower end portion of the main body portion 3 is the portion with the largest outer diameter (the largest outer diameter portion), and the diameter of an annular side portion 32 decreases upward (toward the flange 5). Therefore, when the cap 1 is attached to the tube 6, the entire main body portion 3 does not come into strong contact with the inner circumferential surface of the cylindrical portion 61 of the tube 6, and thus, an attaching operation can be easily performed. When the cap 1 is detached, the upper portion of the main body portion 3 and the inner face of the upper opening portion 63 of the tube 6 are not in intimate contact with each other, and thus, a detachment operation can be easily performed.

The length of the main body portion 3 that extends downward is suitably about 1 to 5 mm, and in particular, suitably 1.2 to 4 mm. Further, the difference between the outer diameter of the largest outer diameter portion of the main body portion 3 and the outer diameter of the smallest diameter portion thereof (a boundary portion between the main body portion 3 and the flange) is preferably 0.1 to 0.3 mm.

Figure 3:
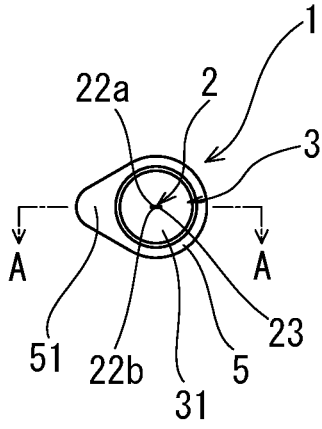
FIG. 3 is a bottom view of the biological sample storage tube cap shown in FIG. 1.

The main body portion 3 includes the flange 5 that is provided at the upper end portion thereof and protrudes laterally outward. In this example, the flange 5 is an annular protruding portion. Further, in the cap 1 of this example, the flange 5 includes an extension portion 51 that partially extends further laterally outward. The extension portion 51 is used as a holding portion when detaching the cap 1 attached to the tube 6. In the cap 1 of this example, as shown in FIG. 3, the extension portion 51 has a substantially triangular shape that has a rounded tip and is tapered toward the tip.

The biological sample adhering portion 2 extends downward from the lower face of the main body portion 3 and is elongated so as to be stored in the tube 6. The biological sample adhering portion 2 is configured such that a leading end portion 23 does not come into contact with an inner face of the bottom portion of the tube 6 in a state in which the cap 1 is attached to the tube 6. In the state in which the cap 1 is attached to the tube 6, the distance between a lower end (leading end) 23 of the biological sample adhering portion 2 and the inner face of the bottom portion of the tube 6 is preferably 1 mm or more, and particularly preferably 3 mm or more.

In the cap 1 of this example, the biological sample adhering portion 2 also includes a leading end portion flat face 22a that extends by a predetermined length. Because the biological sample adhering portion 2 includes the leading end portion flat face 22a, the adhesion of the biological sample is facilitated. Also, in the cap 1 of this example, the biological sample adhering portion 2 has a thin plate shape and includes leading end portion flat faces 22a and 22b on two sides of the leading end portion thereof, and is configured such that a biological sample can adhere to the two sides thereof. Note that the biological sample adhering portion 2 may have a narrow prismatic shape.

Also, the biological sample adhering portion 2 is preferably optically transparent, and particularly preferably includes a transparent leading end portion. Doing this enables confirmation of an adhered biological sample. Also, the biological sample adhering portion 2 preferably has a certain degree of hardness and flexibility. Such a biological sample adhering portion 2 facilitates the operation for adhering a biological sample.

Further, in this example, the biological sample adhering portion 2 of the cap 1 includes the leading end portion 23 whose outer shape becomes smaller toward the leading end. This facilitates insertion of the leading end of the biological sample adhering portion 2 into the tube 6.

The biological sample adhering portion 2 is cuttable using a cutting tool such as a pair of scissors, and a cut piece formed by cutting the biological sample adhering portion 2 falls into the biological sample storage tube 6. The biological sample adhering portion 2 is preferably thin such that it can be cut using a cutting tool such as a pair of scissors. Specifically, the thickness of the biological sample adhering portion 2 is preferably 0.05 to 0.5 mm, and particularly preferably 0.06 to 0.3 mm. Further, the width of the biological sample adhering portion 2 is preferably 0.3 to 2 mm, and particularly preferably 0.4 to 1.5 mm. Note that the biological sample adhering portion 2 may have the above thickness and width at the leading end portion, and a rear end portion may be thicker or wider than the leading end portion. Also, the biological sample adhering portion 2 may become thicker and wider toward the rear end portion.

Semi-hard resin or soft resin is suitable as a material of the biological sample storage tube cap 1. Specifically, it is possible to use polyolefins such as polypropylene and polyethylene, polyolefin elastomers, styrene-based resins such as polystyrene and SBS, polyester resins such as polyethylene terephthalate and polybutylene terephthalate, polyester elastomers, and the like.

Also, in this example, as shown in FIG. 4, the biological sample adhering portion 2 is made of a synthetic resin material that is different from that of the other portions (the main body portion 3) of the cap 1, and a base end portion 21 of the biological sample adhering portion 2 enters the main body portion 3 where it is fixed. Note that the entire cap 1 may be made of the same material into a single body.

When the biological sample adhering portion 2 is made of a synthetic resin material that is different from that of the other portions (the main body portion 3) of the cap 1, it is possible to use, as a material for forming the biological sample adhering portion 2, a material having higher flexibility, or conversely, a material having lower flexibility than the material for forming the other portions. When the biological sample adhering portion 2 is made of a synthetic resin material that is different from that of the other portions (the main body portion 3) of the cap 1, it is preferable to use an insert molding process in which the biological sample adhering portion is molded first and inserted into a mold, and the other part is formed, and a double molding process in which a biological sample adhering portion forming resin is first injected, and a resin for forming the other parts is then injected.

Also, it is preferable that the leading end of the biological sample adhering portion 2 includes a marking for finding the position of the leading end of the biological sample adhering portion 2. It is conceivable that the marking may be made by applying a color (e.g., black, blue, green, or the like) to a front surface, a back surface, or a side surface of the leading end portion 23.

Also, the biological sample storage tube cap 1 of this example includes the biological sample associated information presenting plate-shaped portion 4 that extends upward from the upper face of the main body portion 3 by a predetermined length.

The biological sample associated information presenting plate-shaped portion 4 is a plate-shaped portion that has a predetermined width and extends upward of the upper face of the main body portion 3 substantially perpendicularly thereto. The biological sample associated information presenting plate-shaped portion 4 is able to present biological sample associated information on two sides thereof. Note that a configuration may be employed where biological sample associated information can only be presented on one surface of the biological sample associated information presenting plate-shaped portion 4. Also, the upper end of the biological sample associated information presenting plate-shaped portion 4 has a round shape without any corner portions.

Characters and the like can be written using a writing instrument on the surfaces of flat surface portions 41*a* and 41*b* of the plate-shaped portion 4, and biological sample associated information can be presented thereon. It is conceivable that examples of the biological sample associated information include the subject's name and collection date. Also, the flat surface portions 41*a* and 41*b* of the plate-shaped portion 4 may have rough surfaces, specifically, surfaces having a satin finish. Doing this makes it easier to write using a writing instrument or the like and easier to visually recognize written characters or the like. Also, a sheet printed with biological sample associated information may be adhered to the plate-shaped portion 4. Accordingly, it is possible to present biological sample associated information.

Also, the biological sample associated information presenting plate-shaped portion 4 is preferably configured such that the flat surface portions 41*a* and 41*b* for presenting information are oriented in the same direction as the leading end portion flat faces 22*a* and 22*b* of the biological sample adhering portion 2. When an operation for presenting biological sample associated information is performed first on the plate-shaped portion 4 and an operation for adhering a biological sample to the biological sample adhering portion 2 is then performed, biological sample associated information can be easily confirmed during the adhering operation. Note that the extension portion 51 extends in the same direction as the flat surface portions 41*a* and 41*b* of the biological sample associated information presenting plate-shaped portion 4.

Figure 7:
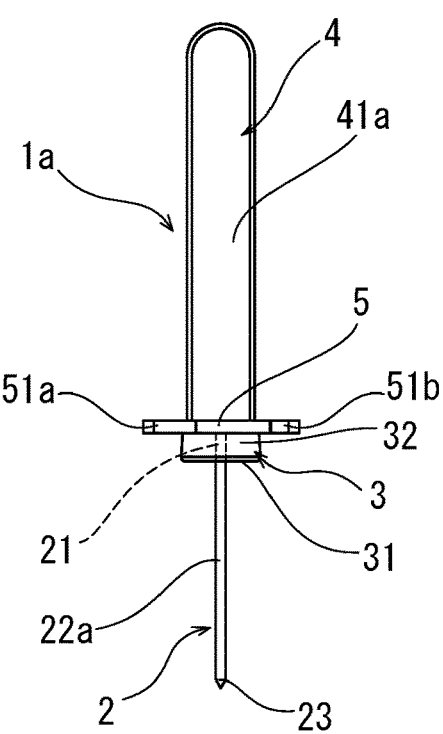
FIG. 7 is a front view of a biological sample storage tube cap according to another example of the present invention.
Figure 8:
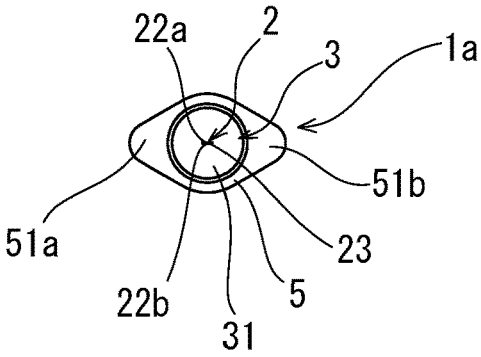
FIG. 8 is a bottom view of the biological sample storage tube cap shown in FIG. 7.

The biological sample storage tube cap according to the present invention may be the biological sample storage tube cap shown in FIGS. 7 and 8. In a biological sample storage tube cap 1*a* of this example, the flange 5 includes two extension portions 51*a* and 51*b* that face each other. This facilitates the operation for detaching a cap 1*a* attached to the tube 6. Note that the extension portions 51*a* and 52*b* extend in the same direction as the flat surfaces of the flat surface portions 41*a* and 41*b* of the biological sample associated information presenting plate-shaped portion 4. Note that the biological sample storage tube cap 1*a* of this example is the same as the biological sample storage tube cap 1 of the above-described example, except that the biological sample storage tube cap 1*a* includes the extension portion 51*b*.

Figure 9:
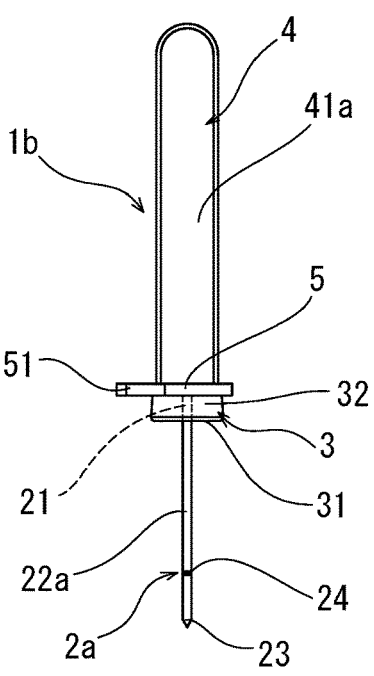
FIG. 9 is a front view of a biological sample storage tube cap according to another example of the present invention.

The biological sample storage tube cap according to the present invention may be the biological sample storage tube cap shown in FIG. 9. A biological sample storage tube cap 1*b* of this example includes a colored marker 24, which is located at a leading end portion of a biological sample adhering portion 2*a* and is provided on the base end side relative to the leading end of the biological sample adhering portion 2*a* by a predetermined length. As a result, the leading end portion to which a biological sample is adhered can be easily recognized. The colored marker can also be used as an indicator when cutting the biological sample adhering portion 2*a*.

As for the colored marker, a circular mark, a polygonal (e.g., triangular) mark, or the like may be used in addition to the line-shaped marker shown in FIG. 9. It is possible to use black, blue, green, or the like as the colored marker, for example. The position of the colored marker 24 is preferably located 3 to 10 mm, and particularly preferably located 4 to 8 mm from the leading end of the biological sample adhering portion 2*a*. Note that the biological sample storage tube cap 1*b* of this example is the same as the biological sample storage tube cap 1 of the above-described example, except that the biological sample storage tube cap 1*b* includes the colored marker 24.

Figure 10:
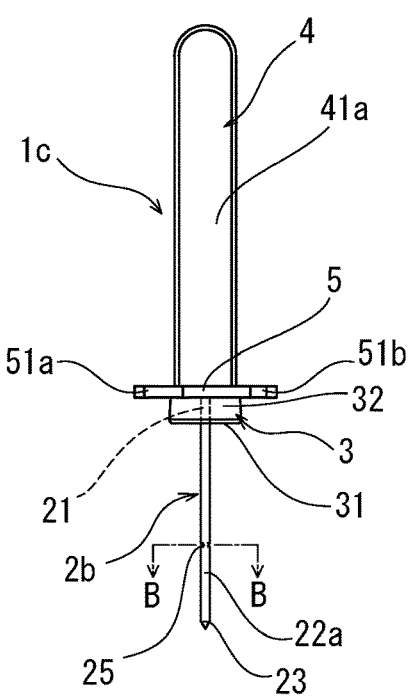
FIG. 10 is a front view of a biological sample storage tube cap according to another example of the present invention.
Figure 11:
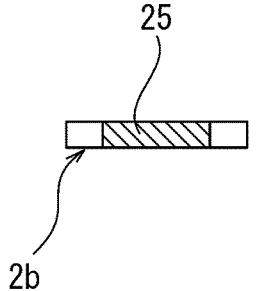
FIG. 11 is an enlarged cross-sectional view taken along line B-B in FIG. 10.

The biological sample storage tube cap according to the present invention may be the biological sample storage tube cap shown in FIGS. 10 and 11. A biological sample storage tube cap 1*c* of this example includes an easily cuttable portion 25, which is located at a leading end portion of a biological sample attachment portion 2*b* and is provided on the base end side relative to the leading end of the biological sample attachment portion 2*b* by a predetermined length. As a result, the leading end portion to which a biological sample is adhered can be easily recognized. The easily cuttable portion 25 can also function as an indicator when cutting the biological sample attachment portion 2*b*. In this example, the easily cuttable portion 25 is formed by making a cut in a side portion of the biological sample adhering portion 2*b*. Specifically, the easily cuttable portion 25 is formed by making two cuts in the side portions of the biological sample adhering portion 2*b* such that the two cuts face each other. Therefore, as shown in FIGS. 10 and 11, the width of the biological sample adhering portion 2*b* is narrow and the biological sample adhering portion 2*b* can be easily cut at the portion where the easily cuttable portion 25 is formed. A notch that forms the easily cuttable portion 25 may have a semicircular shape, a triangular shape, or the like, in addition to a rectangular shape shown in the drawings.

Also, a colored marker may be provided on the easily cuttable portion 25. It is possible to use black, blue, green, or the like as the colored marker, for example. The position of the easily cuttable portion 25 is preferably located 3 to 10 mm, and particularly preferably located 4 to 8 mm from the leading end of the biological sample adhering portion 2*b*. Note that the biological sample storage tube cap 1*c* of this example is the same as the biological sample storage tube cap 1 of the above-described example, except that the biological sample storage tube cap 1*c* includes the easily cuttable portion 25.

Figure 12:
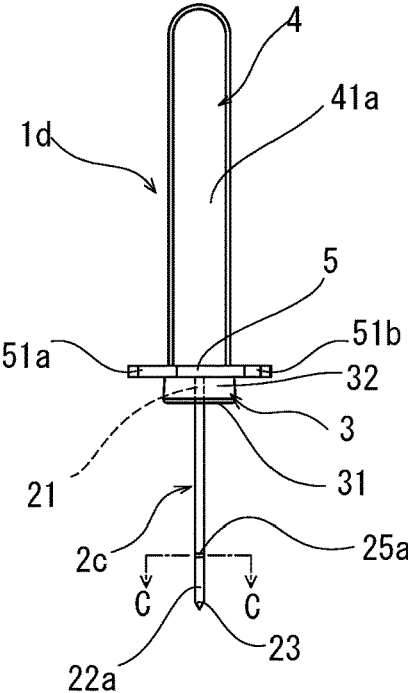
FIG. 12 is a front view of a biological sample storage tube cap according to another example of the present invention.
Figure 13:
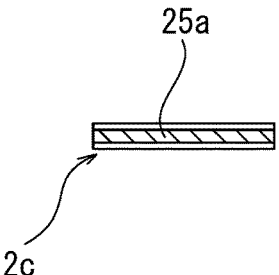
FIG. 13 is an enlarged cross-sectional view taken along line C-C in FIG. 12.

The form of the easily cuttable portion 25 is not limited to the above, and may be the form shown in FIGS. 12 and 13, for example. In a biological sample storage tube cap 1*d* of this example, an easily cuttable portion 25*a* is formed by a thin linear portion of a biological sample adhering portion 2c. Specifically, the easily cuttable portion 25a is formed by linear recesses formed on two sides of the biological sample adhering portion 2c. Therefore, as shown in FIGS. 12 and 13, the biological sample adhering portion 2c is thin and can be easily cut at the portion where the easily cuttable portion 25a is formed.

Also, a colored marker may be provided on the easily cuttable portion 25a. It is possible to use black, blue, green, or the like as the colored marker, for example. The position of the easily cuttable portion 25a is preferably located 3 to 10 mm, and particularly preferably located 4 to 8 mm from the leading end of the biological sample adhering portion 2c.

Figure 14:
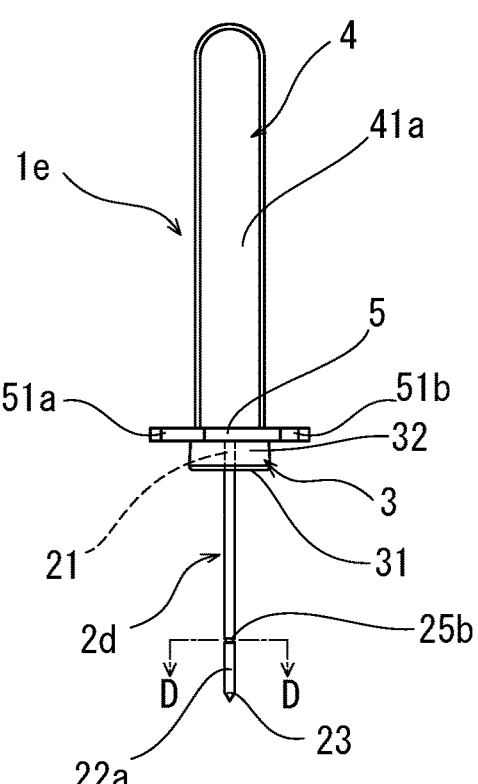
FIG. 14 is a front view of a biological sample storage tube cap according to another example of the present invention.
Figure 15:
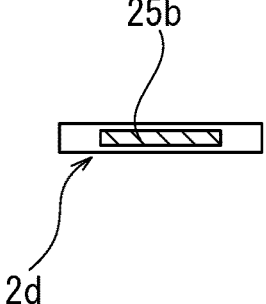
FIG. 15 is an enlarged cross-sectional view taken along line D-D in FIG. 14.

Also, the form of the easily cuttable portion 25b may be the form shown in FIGS. 14 and 15. In a biological sample storage tube cap 1e of this example, an easily cuttable portion 25b is formed by making cuts in a biological sample adhering portion 2d and a thin linear portion. Specifically, the easily cuttable portion 25b is formed by making two cuts in the side portions of the biological sample adhering portion 2d such that the two cuts face each other and linear recesses formed on two sides of the biological sample adhering portion 2d. Therefore, as shown in FIGS. 14 and 15, the biological sample adhering portion 2d is thin and narrow, and the biological sample adhering portion 2d can be easily cut at the portion where the easily cuttable portion 25b is formed.

Also, a colored marker may be provided on the easily cuttable portion 25b. It is possible to use black, blue, green, or the like as the colored marker, for example. The position of the easily cuttable portion 25b is preferably located 3 to 10 mm, and particularly preferably located 4 to 8 mm from the leading end of the biological sample adhering portion 2d.

Figure 16:
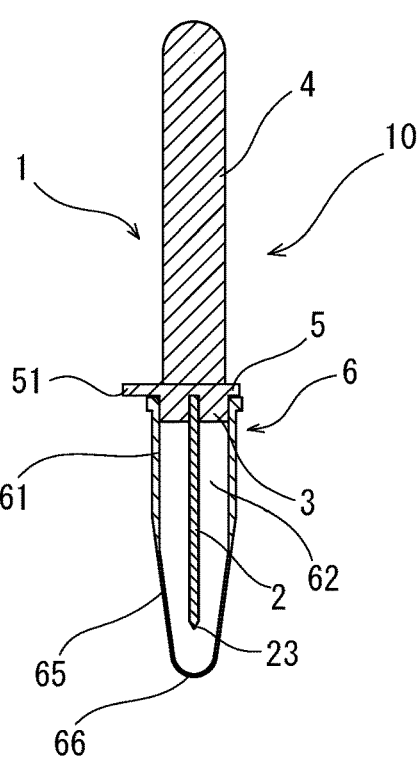
FIG. 16 is a cross-sectional view illustrating a state in which the biological sample storage tube cap shown in FIG. 1 is attached to the biological sample storage tube.
Figure 17:
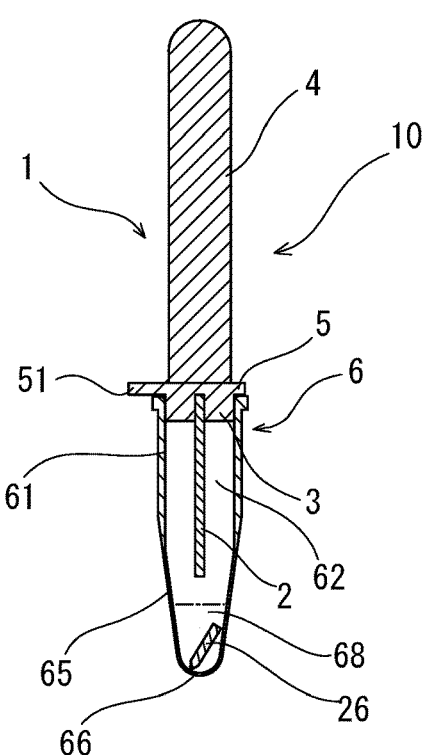
FIG. 17 is a diagram illustrating effects of a biological sample storage container provided with a biological sample storage tube cap according to the present invention.

Next, a biological sample storage tube cap according to the present invention and effects of a biological sample storage container provided with the same will be described with reference to FIGS. 1, 16, and 17.

First, a biological sample (e.g., cells of an artificially fertilized ovum) is collected using a sample collecting tool (e.g., a micropipette) and adhered to the leading end portion flat face 22a of the biological sample adhering portion 2 of the biological sample storage tube cap 1, the biological sample adhering portion 2 to which the biological sample has been adhered is inserted into the biological sample storage tube 6, the biological sample is stored by attaching the main body portion 3 to the opening portion of the tube 6 so as to close the tube 6, thus sealing the biological sample storage container. Then, if necessary, biological sample associated information (e.g., the subject's name, collection date, and the like) is directly written on the biological sample associated information presenting plate-shaped portion 4, or a sheet labeled with biological sample associated information (e.g., the subject's name, collection date, and the like) is attached thereto, and then the biological sample storage container is transferred to a testing facility.

At the testing facility, the sealed biological sample storage container is opened by pushing up the extension portion 51 of the flange 5 of the cap 1 from below, and the cap 1 is separated from the tube 6. Then, if necessary, the biological sample adhering portion 2 is cut using a cutting tool in a state in which the leading end portion flat face 22a to which the biological sample of the biological sample adhering portion 2 has been adhered is positioned near the upper opening portion 63 of the tube 6. As shown in FIG. 17, a cut piece 26 formed by cutting the biological sample adhering portion 2 falls and is stored in the tube 6. Also, if necessary, a test liquid 68 is injected into the tube 6, and the cap 1 is attached to the tube 6 again so as to close the tube 6. The cut piece 26 to which the biological sample has been adhered is located in the test liquid 68.

Figure 18:
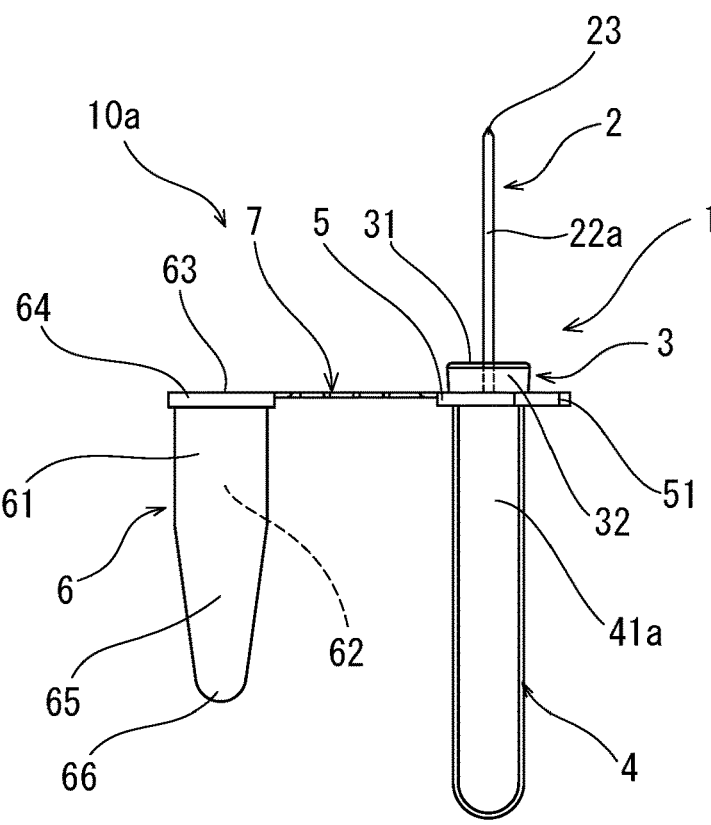
FIG. 18 is a front view of a biological sample storage container provided with a biological sample storage tube cap according to another example of the present invention.

Next, a biological sample storage container 10a according to another example of the present invention shown in FIGS. 18 to 20 will be described. In the biological sample storage container 10a of this example, the biological sample storage tube 6 and the biological sample storage tube cap 1 are connected to each other by a connection portion 7.

The biological sample storage container 10a of this example includes the connection portion 7 that connects an upper portion of the biological sample storage tube 6 and an upper portion of a main body portion 3 of the biological sample storage tube cap 1 to each other. The above-described tube can be used as the tube 6. Although the above-described biological sample storage tube cap 1 is used as a biological sample storage tube cap, it is also possible to use all of the biological sample storage tube caps of the above-described examples.

In the biological sample storage container 10a of this example, one end of the connection portion 7 is fixed to a side face of the annular rib 64 of the tube 6, and the other end thereof is fixed to a side face of the flange 5 of the cap 1. The fixed portion of the connection portion 7 that is fixed to the cap 1 is provided at a position so as to oppose an extension portion 51 of the flange 5. Thus, the fixed portion does not hinder an operation performed using the extension portion 51. Therefore, in the biological sample storage container 10a of this example, the extension portion 51 of the flange 5 faces a direction opposite to the tube 6.

Also, the connection portion 7 in this example has flexibility, includes at least one bent portion or curved portion, and is stretchable. In the biological sample storage container 10a of this example, the tube 6 and the cap 1 do not separate from each other due to the connection portion 7, and the connection portion 7 does not hinder attachment of the cap 1 to the tube 6. Note that the connection portion 7 may be cuttable using a cutting tool.

Figure 19:
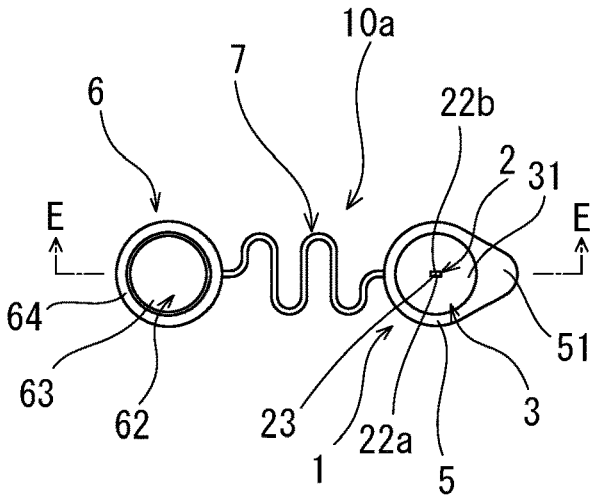
FIG. 19 is a plan view of the biological sample storage container shown in FIG. 18.
Figure 20:
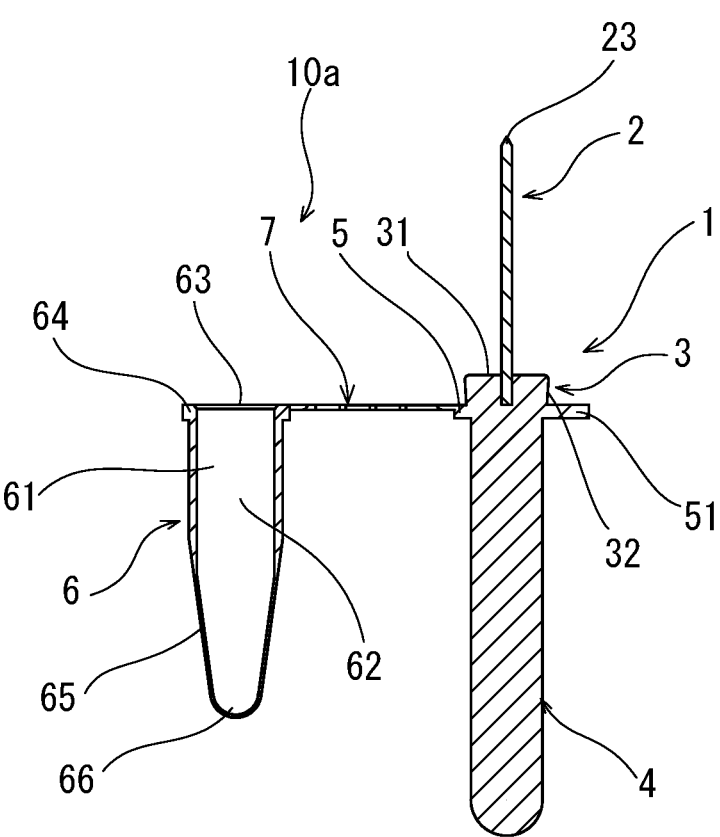
FIG. 20 is a longitudinal cross-sectional view of the biological sample storage container shown in FIG. 18.

As shown in FIG. 19, the connection portion 7 of this example has a wavy shape provided with a plurality of curved portions. The distance between one end and the other end of the connection portion 7 (in other words, the separation distance between the tube 6 and the cap 1) is suitably 5 to 20 mm, and in particular, suitably 7 to 15 mm. Also, the connection portion 7 is formed by a linear body having a rectangular or circular cross-section. The width or diameter of the linear body of the connection portion 7 is preferably about 0.3 to 2 mm.

It is preferable that the connection portion 7 is formed as a single body with the main body portion 3 having at least the flange 5 of the biological sample storage tube cap and the tube 6. It is possible to use, as a material for forming the main body portion 3 having at least the flange 5 of the biological sample storage tube cap, the tube 6, and the connection portion 7, polyolefins such as polypropylene and polyethylene, polyolefin elastomers, styrene-based resins such as polystyrene and SBS, polyester resins such as polyethylene terephthalate and polybutylene terephthalate, polyester elastomers, and the like.

INDUSTRIAL APPLICABILITY

The biological sample storage tube cap according to the present invention is as described below.

(1) A biological sample storage tube cap comprising:
a main body portion;
an elongated biological sample adhering portion that extends downward from a lower face of the main body portion; and
a flange that protrudes laterally outward from the main body portion,
wherein the biological sample storage tube cap is to be attached to a hollow biological sample storage tube having a lower closed portion and an upper opening portion, and that is for closing the upper opening portion,
the main body portion is configured to enter the upper opening portion of the biological sample storage tube and close the upper opening portion, and
the biological sample adhering portion is enterable in the biological sample storage tube and cuttable and a cut piece formed by cutting of the biological sample adhering portion can fall into the biological sample storage tube.

According to this biological sample storage tube cap, a biological sample can be reliably stored in the tube by adhering the biological sample to the biological sample adhering portion of the cap and attaching the cap to the tube. Further, because the tube is sealed simultaneously with attachment of the cap to the tube, contamination can be suppressed.

Further, the above embodiments may be as described below.

(2) The biological sample storage tube cap according to (1), further comprising a biological sample associated information presenting plate-shaped portion that extends upward from an upper face of the main body portion by a predetermined length.

(3) The biological sample storage tube cap according to (1) or (2),
wherein the biological sample storage tube is a sample storage tube for testing a chromosome of an in vitro fertilized ovum, and the biological sample adhering portion is a cell adhering portion for a cell derived from the in vitro fertilized ovum.

(4) The biological sample storage tube cap according to (1) or (2),
wherein the biological sample storage tube is a biological sample storage tube for PCR, and the biological sample adhering portion is a biological sample adhering portion for PCR.

(5) The biological sample storage tube cap according to any one of (1) to (4), wherein the biological sample adhering portion includes a leading end portion flat face that extends by a predetermined length.

(6) The biological sample storage tube cap according to any one of (1) to (5), wherein the main body portion has a short columnar or cylindrical shape, and a diameter of the main body portion increases toward the leading end thereof.

(7) The biological sample storage tube cap according to any one of (1) to (6), wherein the main body portion and the biological sample adhering portion are made of different synthetic resin materials, and a base end portion of the biological sample adhering portion enters the main body portion where the base end portion is fixed.

The biological sample storage container according to the present invention is as described below.

(8) A biological sample storage container comprising:
a hollow biological sample storage tube having a lower closed portion and an upper opening portion; and
a biological sample storage tube cap for closing the upper opening portion,
wherein the biological sample storage tube cap is the biological sample storage tube cap according to any one of (1) to (7).

Further, the above embodiments may be as described below.

(9) The biological sample storage container according to (8), further comprising a connection portion that connects an upper portion of the biological sample storage tube and an upper portion of the main body portion of the biological sample storage tube cap to each other.

The invention claimed is:

1. A biological sample storage tube cap comprising:
a main body portion that has a lower face and an upper face arranged parallel in a vertical direction and oriented oppositely;
an elongated biological sample adhering portion that extends downward in the vertical direction from the lower face of the main body portion; and
a flange that protrudes outward from the main body portion in a radial direction, which is perpendicular to the vertical direction,
wherein the biological sample storage tube cap is to be attached to a hollow biological sample storage tube having a lower closed portion and an upper opening portion, and that is for closing the upper opening portion,
the main body portion is configured to enter the upper opening portion of the biological sample storage tube and close the upper opening portion,
the biological sample adhering portion is enterable in the biological sample storage tube and cuttable and a cut piece formed by cutting of the biological sample adhering portion can fall into the biological sample storage tube,
the biological sample adhering portion has a plate shape such that two flat faces are provided on two sides of the plate shape wherein normal vectors of the flat faces are defined as being oriented in a thickness direction of the biological sample adhering portion, the thickness direction is perpendicular to the vertical direction, and a thickness of the biological sample adhering portion measured in the thickness direction is 0.05 to 0.5 mm,
the biological sample storage tube cap has a biological sample associated information presenting plate-shaped portion that extends upward from the upper face of the main body portion in the vertical direction by a predetermined length wherein the plate-shaped portion has flat surface portions of which surfaces are flat and of which normal vectors are oriented in the same direction as the thickness direction of the biological sample adhering portion, and
the flange includes an extension portion that partially extends further laterally outward, and the extension portion extends in the same direction as the flat surface portions of the biological sample associated information presenting plate-shaped portion.

2. The biological sample storage tube cap according to claim 1,
wherein the biological sample storage tube is a sample storage tube for testing a chromosome of an in vitro fertilized ovum, and the biological sample adhering portion is a cell adhering portion for a cell derived from the in vitro fertilized ovum.

3. The biological sample storage tube cap according to claim 1, wherein the biological sample storage tube is a biological sample storage tube for polymerase chain reaction, and the biological sample adhering portion is a biological sample adhering portion for the polymerase chain reaction.

4. The biological sample storage tube cap according to claim 1, wherein the main body portion has a columnar shape or a cylindrical shape, with a length of 1 to 5 mm, and a diameter of the main body portion increases toward a leading end of the main body portion.

5. The biological sample storage tube cap according to claim 1, wherein the main body portion and the biological sample adhering portion are made of different synthetic resin materials, and a base end portion of the biological sample adhering portion enters the main body portion where the base end portion is fixed.

6. The biological sample storage tube cap according to claim 1, wherein the elongated biological sample adhering portion has an easily cuttable portion formed by making a cut in a side portion of the elongated biological sample adhering portion or a linear recess formed on the elongated biological sample adhering portion.

7. The biological sample storage tube cap according to claim 6, wherein the easily cuttable portion has a colored marker.

8. The biological sample storage tube cap according to claim 1, wherein the biological sample adhering portion includes a leading end whose outer shape becomes smaller toward the leading end.

9. The biological sample storage tube cap according to claim 1, wherein the biological sample adhering portion includes a leading end portion whose outer shape becomes smaller toward the leading end and a marking, and the marking is made by applying a color to a front surface, a back surface, or a side surface of the leading end portion.

10. The biological sample storage tube cap according to claim 1, wherein the main body portion has a lower end portion, and the lower end portion has largest outer diameter among the main body portion, and the diameter of the main body portion decreases toward the flange from the lower end portion.

11. A biological sample storage container comprising:

a hollow biological sample storage tube having a lower closed portion and an upper opening portion; and a biological sample storage tube cap for closing the upper opening portion, wherein the biological sample storage tube cap is the biological sample storage tube cap according to claim 1.

12. The biological sample storage container according to claim 11, further comprising a connection portion that connects an upper portion of the biological sample storage tube and an upper portion of the main body portion of the biological sample storage tube cap to each other.

13. The biological sample storage tube cap according to claim 1, wherein a width of the biological sample adhering portion, which is measured in the width direction, is larger than the thickness of the biological sample adhering portion.

14. The biological sample storage tube cap according to claim 13, wherein the width of the biological sample adhering portion is 0.3 to 2 mm.

15. The biological sample storage tube cap according to claim 1, wherein the extension portion extends in the same side as the flat surface portions of the biological sample associated information presenting plate-shaped portion.

16. A biological sample storage tube cap comprising:

a main body portion that has a lower face and an upper face arranged parallel in a vertical direction and oriented oppositely;

an elongated biological sample adhering portion that extends downward in the vertical direction from the lower face of the main body portion;

a biological sample associated information presenting plate-shaped portion that extends upward in the vertical direction from the upper face of the main body portion by a predetermined length; and a flange that protrudes outward from the main body portion in a radial direction, which is perpendicular to the vertical direction, wherein the biological sample storage tube cap is to be attached to a hollow biological sample storage tube having a lower closed portion and an upper opening portion, and that is for closing the upper opening portion, the main body portion is configured to enter the upper opening portion of the biological sample storage tube and close the upper opening portion, the biological sample adhering portion is enterable in the biological sample storage tube and cuttable and a cut piece formed by cutting of the biological sample adhering portion can fall into the biological sample storage tube, the biological sample adhering portion includes a leading end portion whose outer shape becomes smaller toward the leading end, the main body portion and the biological sample adhering portion are made of different synthetic resin materials, and a base end portion of the biological sample adhering portion enters the main body portion where the base end portion is fixed, the biological sample adhering portion has a plate shape such that two flat faces are provided on two sides of the plate shape wherein normal vectors of the flat faces are defined as being oriented in a thickness direction of the biological sample adhering portion, the thickness direction is perpendicular to the vertical direction, and a thickness of the biological sample adhering portion measured in the thickness direction is 0.05 to 0.5 mm, the biological sample associated information presenting plate-shaped portion has flat surface portions of which surfaces are flat and of which normal vectors are oriented in the same direction as the thickness direction of the biological sample adhering portion, a width of the biological sample adhering portion, which is measured in the width direction, is larger than the thickness of the biological sample adhering portion, and the width of the biological sample adhering portion is 0.3 to 2 mm.

17. A biological sample storage tube cap comprising:

a main body portion that has a lower face and an upper face arranged parallel in a vertical direction and oriented oppositely;

an elongated biological sample adhering portion that extends downward in the vertical direction from the lower face of the main body portion;

a biological sample associated information presenting plate-shaped portion that extends upward in the vertical direction from the upper face of the main body portion by a predetermined length; and a flange that protrudes outward from the main body portion in a radial direction, which is perpendicular to the vertical direction, wherein the biological sample storage tube cap is to be attached to a hollow biological sample storage tube having a lower closed portion and an upper opening portion, and that is for closing the upper opening portion, the main body portion is configured to enter the upper opening portion of the biological sample storage tube and close the upper opening portion, the biological sample adhering portion is enterable in the biological sample storage tube and cuttable and a cut piece formed by cutting of the biological sample adhering portion can fall into the biological sample storage tube, the biological sample adhering portion includes a leading end portion whose outer shape becomes smaller toward the leading end, the main body portion has a lower end portion, and the lower end portion has largest outer diameter among the main body portion, and the diameter of the main body portion decreases toward the flange from the lower end portion, the main body portion and the biological sample adhering portion are made of different synthetic resin materials, and a base end portion of the biological sample adhering portion enters the main body portion where the base end portion is fixed, the biological sample adhering portion has a plate shape such that two flat faces are provided on two sides of the plate shape wherein normal vectors of the flat faces are defined as being oriented in a thickness direction of the biological sample adhering portion, the thickness direction is perpendicular to the vertical direction, and a thickness of the biological sample adhering portion measured in the thickness direction is 0.05 to 0.5 mm, and the biological sample storage tube cap has a biological sample associated information presenting plate-shaped portion that extends upward from the upper face of the main body portion in the vertical direction by a predetermined length wherein the plate-shaped portion has flat surface portions of which surfaces are flat and of which normal vectors are oriented in the same direction as the thickness direction of the biological sample adhering portion.

* * * * *